United States Patent [19]
Guay et al.

[11] Patent Number: 5,937,874
[45] Date of Patent: *Aug. 17, 1999

[54] DENTAL FLOSS HAVING TWO COMPONENTS WHICH REACT TO FORM AN ACTIVE AGENT

[75] Inventors: Gordon G. Guay, Chelmsford; Jean L. Spencer, Boston, both of Mass.

[73] Assignee: Gillette Canada Inc., Kirkland, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/868,118

[22] Filed: Jun. 3, 1997

[51] Int. Cl.⁶ .................................................. A61C 15/00
[52] U.S. Cl. ............................................ 132/321; 424/401
[58] Field of Search ..................... 132/321, 329; 424/401, 53, 57

[56] References Cited

U.S. PATENT DOCUMENTS

| | | | |
|---|---|---|---|
| 4,654,256 | 3/1987 | Doree et al. | 428/304.4 |
| 4,986,288 | 1/1991 | Kent et al. | 132/321 |
| 5,000,941 | 3/1991 | Chernack | 424/49 |
| 5,098,711 | 3/1992 | Hill et al. | 424/401 |
| 5,211,939 | 5/1993 | Turesky et al. | 424/49 |
| 5,238,749 | 8/1993 | Cueman et al. | 428/441 |
| 5,250,288 | 10/1993 | Turesky et al. | 424/49 |
| 5,300,290 | 4/1994 | Spencer | 424/54 |
| 5,320,842 | 6/1994 | Spencer | 424/401 |
| 5,357,989 | 10/1994 | Gathani | 132/321 |
| 5,362,424 | 11/1994 | Lee et al. | 264/4.3 |
| 5,392,795 | 2/1995 | Gathani | 132/323 |
| 5,403,578 | 4/1995 | Gordon | 424/53 |

FOREIGN PATENT DOCUMENTS

| | | |
|---|---|---|
| 0 696 450 A1 | 2/1996 | European Pat. Off. . |
| 2 258 402 | 2/1993 | United Kingdom . |
| WO 96/39117 | 12/1996 | WIPO . |

*Primary Examiner*—Todd E. Manahan
*Attorney, Agent, or Firm*—Fish & Richardson P.C.

[57] ABSTRACT

A dental hygiene article that includes a dental floss, a first component associated with the floss, a second component associated with the floss, and a first barrier constructed to separate the first component from the second component until flossing occurs. The first and the second components are selected to react with each other when the first and the second components are combined, e.g., in the mouth during flossing.

37 Claims, 2 Drawing Sheets

DENTAL FLOSS HAVING TWO COMPONENTS WHICH REACT TO FORM AN ACTIVE AGENT

BACKGROUND OF THE INVENTION

The invention relates to a dental hygiene article.

Delivering therapeutic agents to the mouth to decrease tooth decay and periodontal diseases caused by the presence of bacteria in the mouth has been the focus of people in the health care fields. Frequently these agents are delivered to the mouth via mouthwash, toothpaste and dental floss. It is difficult, however, to apply these agents to the interdental and subgingival regions of the mouth. It is also difficult to control the quantity of agent applied to the mouth and to maintain an effective concentration of these agents in the mouth over a period of time. In addition, certain types of agents that are not stable over time are even more difficult to deliver to the mouth using these methods.

SUMMARY OF THE INVENTION

In one aspect, the invention features a dental hygiene article that includes a dental floss, a first component associated with the floss, a second component associated with the floss, and a first barrier constructed to separate the first component from the second component until flossing occurs. The first and the second components are selected to react with each other when the first and the second components are combined. Preferably the first and the second components are capable of reacting with each other to form an active agent, i.e., an agent capable of performing one or more functions within the mouth, such as, e.g., a therapeutic agent, a gas, (e.g., carbon dioxide or oxygen), a buffer, an exclusion barrier, e.g., a film, or heat.

A third component is essentially simultaneously created and applied to an oral surface by virtue of the in situ reaction between the first and second components. The in situ reaction thus enables the application of components that are prone to rapid dissipation such as, e.g., oxygen gas and carbon dioxide gas, to an oral surface. Examples of suitable two component systems include zinc bicarbonate and citric acid, calcium and phosphate salts, and peroxide and bicarbonate compounds.

In preferred embodiments, the barrier is a microcapsule in which the first component is encapsulated. Preferably the microcapsule is constructed to release the first component upon the application of a force to the floss to allow the first component to contact the second component. The microcapsule can also be water soluble. Alternatively, the barrier is a water soluble binder associated with the first component in a manner to prevent the first component from contacting the second component. The first component is preferably incorporated into the binder.

The dental hygiene article preferably further includes a second barrier constructed to separate the second component from the first component. In preferred embodiments, the second barrier is a microcapsule in which the second component is encapsulated. Alternatively, the second barrier is a water soluble binder associated with the second component in a manner to prevent the second component from contacting the first component. The second component is preferably incorporated into the binder. The dental hygiene article may further include a first coloring agent encapsulated within the first microcapsule and a second coloring agent encapsulated within the second microcapsule.

In another embodiment, the dental hygiene article includes a water insoluble barrier associated with the floss. Preferably the water insoluble barrier is coated over the first and second components so as to protect the components and the barriers from moisture such as, e.g., the moisture present during the manufacture or storage of the dental hygiene article.

In other embodiments, the dental hygiene article includes a first barrier that includes a wall defining a first lumen and, optionally, a second barrier that includes a wall defining a second lumen. The first and second components may be disposed within the first and second barriers.

In another aspect, the invention features a method of manufacturing a dental hygiene article that includes associating a first component with a dental floss, associating a second component with the dental floss, selecting the first and second components to react with each other when the first and second components are combined, and separating the first and second components by providing a barrier that is constructed to separate the first and second components until flossing occurs.

In a further aspect, the invention features a method of flossing an interdental region of a mammal that includes placing a portion of the above-described dental hygiene article in an interdental region and flossing the region with the portion of the dental hygiene article.

In a still further aspect, the invention features a method of generating an active agent in the mouth that includes placing a portion of the above-described dental hygiene article in an interdental region of a mammal and flossing the region with the portion of the article to release the first and the second components, which allows the first and the second components to contact each other and react with each other to form the active agent. Preferably the active agent is selected from the group consisting of a therapeutic agent, a gas (e.g., carbon dioxide and oxygen), a buffer, an exclusion barrier, and heat.

The term "dental floss," as used herein, can mean any elongated flexible article used to cleanse the interdental regions of the mouth including, for example, monofilament, multifilament, bulked, and wax coated dental floss, and dental tape.

The term "microcapsule," as used herein, refers to a hollow capsule having a diameter of less than about 2000 μm.

Other features and advantages of the invention will be apparent from the following description of the preferred embodiments thereof, and from the claims.

DESCRIPTION OF THE PREFERRED EMBODIMENTS

Figure 1:
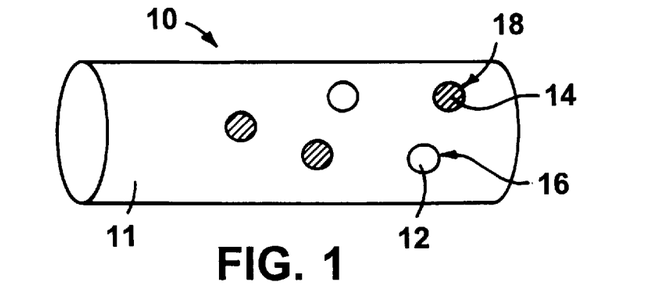
FIG. 1 is a highly enlarged schematic perspective view of a segment of a dental floss according to one embodiment of the invention.

Referring to FIG. 1, dental hygiene article 10 includes two components 12 and 14 distributed randomly on dental floss 11. Components 12, 14 are encapsulated in separate microcapsules 16, 18 so that the two components are separated from each other by microcapsule walls.

Microcapsules 16, 18 function to separate the first and second components so as to prevent the components from contacting each other and reacting with each other until such reaction is desired (i.e., until flossing occurs). Microcapsules 16, 18 are preferably pressure rupturable, i.e., they have walls that are thin enough to rupture upon the application of shear forces of the magnitude generally exerted by flossing, yet of sufficient strength to withstand normally applied pressure occurring during manufacturing, handling and packaging of the dental hygiene article. Preferred microcapsules rupture under normal flossing forces. Microcapsules 16, 18 may also be water soluble so as to release the components by dissolving in water.

Any suitable material capable of forming a microcapsule may be used, provided it is suitable for use in the mouth and non-toxic when used in quantities contemplated by the invention. Examples of suitable materials for forming microcapsules include, but are not limited to, the following: starches; dextrin; gelatin; gum arabic; casein; paraffin wax; natural waxes such as carnauba wax, beeswax, candelilla wax, Japan wax; styrene maleic acid; polyethylene-ethyl cellulose mixtures; cellulose acetophthalate; polymerized acrylonitrile; butadiene and styrene polymers; acetal copolymers and homopolymers; acrylic resins; allylic resins; amino resins; cellulosic resins; epoxy resins; fluoroplastic resins; furan polymers; ionomer resins; nitrile barrier resins; nylon polymers; phenolic resins; phenylene-oxide based resins; poly (amide-imide) resins; polyaryl ethers; polyaryl sulfones; polybutylenes; polycarbonates; polyesters; polyethersulfones; polyethylenes; polyamides; polyimides; polyphenylene sulfides; polypropylenes; polysulfones; polyurethanes; polyvinyl polymers and resins; silicones; gelatin derivatives of which gelatin is the main radical; poly(oxymethylene urea); melamine modified poly (oxymethylene urea); colloidal albumins; hydrolyzed polyvinyl acetate; hydrolysed cellulose esters, e.g., cellulose acetate hydrolysed to acetyl content of 19 to 26 percent; polyvinyl alcohol; vinyl alcohol polymers containing urethane carboxylic acid groups, polymer materials resulting from polymerizing proteins with monomers having a vinyl group; and naturally occurring and synthetic alginates, and combinations and mixtures thereof.

Preferred microcapsules are formed from materials including: starch, gelatin, xanthan gum, poly(oxymethylene urea), and melamine modified poly(oxymethylene urea). Starch, gelatin, and poly(oxymethylene urea) microcapsules are available from a number of sources, e.g., Lipo Technologies of Vadalia, Ohio, Ronald T. Dodge, Co. of Dayton, Ohio, and Minnesota Mining and Manufacturing of St. Paul, Minn. Suitable microcapsules may assume various shapes such as spherical, globular, kidney-like, and rice-like. Preferred microcapsules are spherical and have a diameter ranging from about 1 to about 1000 $\mu$m, more preferably less than about 100 $\mu$m.

Methods of encapsulating components into microcapsules include, polycondensation, interfacial polymerization, coacervation/phase separation, congealable disperse phase encapsulation, solvent dehydration, in situ polymerization, meltable dispersion, solvent evaporation, fluidized-bed coating, air suspension coating, spray coating, spray drying, spray congealing, spray chilling, spin coating, vacuum coating, electrostatic aerosol, centrifugal multi-orifice, and liposome entrapment. These methods are well known in the art, and are disclosed, for example, in U.S. Pat. Nos. 3,324,500, 3,472,675, 3,598,123, 3,640,629 and 5,403,578.

Figure 3:
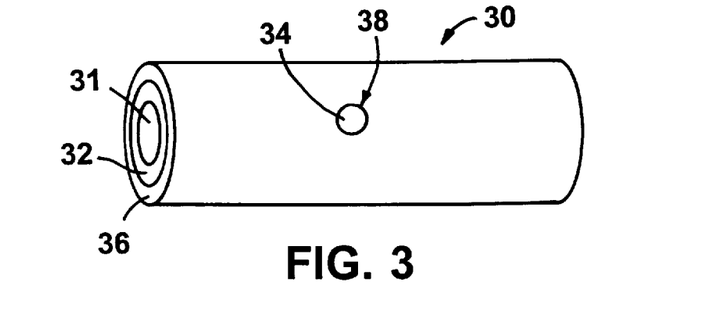
FIG. 3 is a highly enlarged schematic perspective view of a segment of a dental floss according to another alternative embodiment of the invention.
Figure 4:
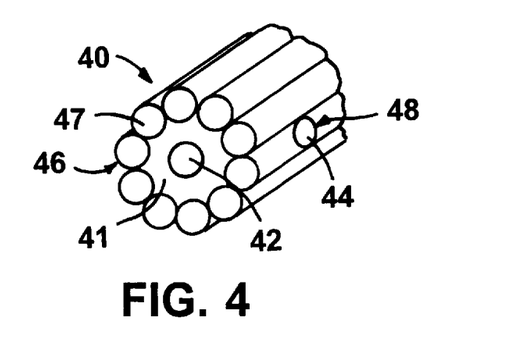
FIG. 4 is a highly enlarged schematic perspective view of a segment of a dental floss according to another alternative embodiment of the invention.
Figure 5:
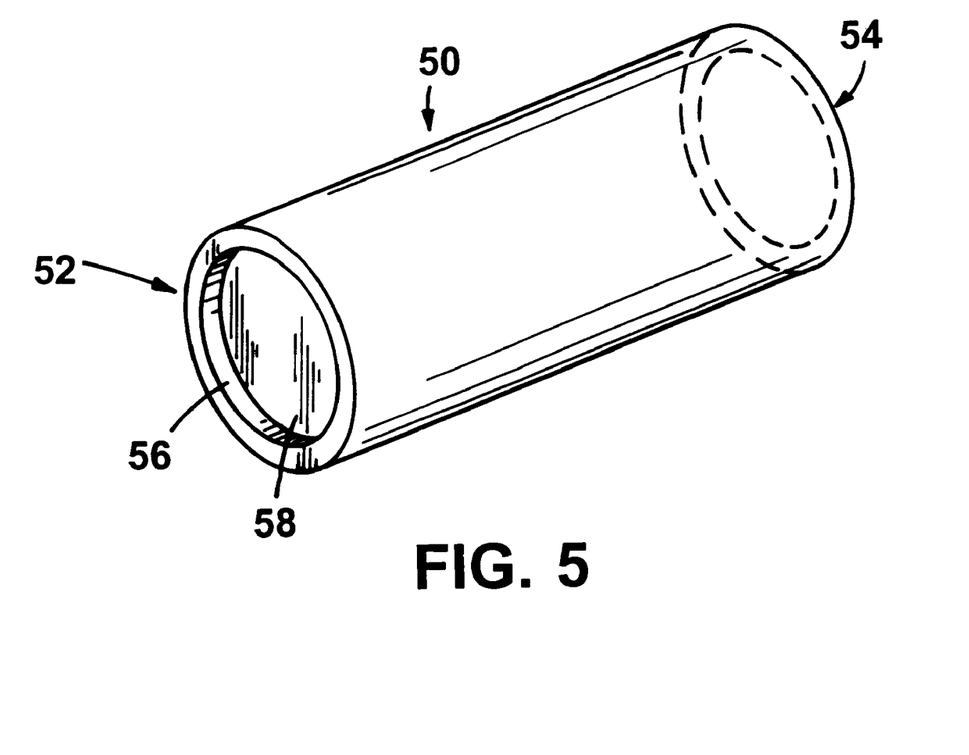
FIG. 5 is a highly enlarged schematic perspective view of a segment of a dental floss according to another alternative embodiment of the invention.

Although barriers in the form of microcapsules are preferred, the barriers may be in any form that will allow the components to remain associated with the floss and that will separate one component from another so as to inhibit the two components from reacting with each other until such time as a reaction is desired. Examples of suitable forms of barriers include microcapsules as shown in FIG. 1, layers as shown in FIG. 2, combinations of layers and microcapsules as shown in FIG. 3, and hollow fiber floss as shown in FIG. 4 and FIG. 5.

Figure 2:
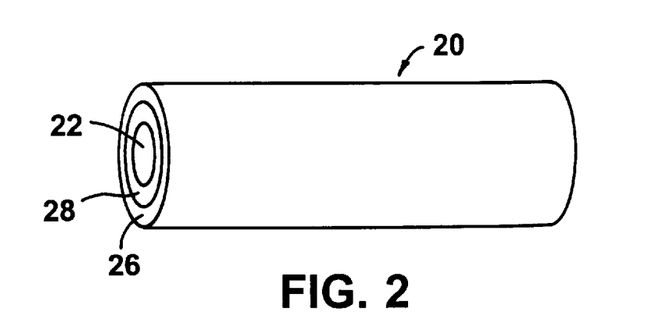
FIG. 2 is a highly enlarged schematic perspective view of a segment of a dental floss according to an alternative embodiment of the invention.

Referring to FIG. 2, dental hygiene article 20 includes barriers in the form of layers 26, 28 on the surface of dental floss 22. One component (not shown) is incorporated into layer 26 and another component (not shown) is incorporated into layer 28. Alternatively, one component may be sandwiched between floss 22 and layer 26 and a second component may be sandwiched between layer 26 and layer 28, thereby preventing the components from reacting with each other. The layers may be continuous or discontinuous and may be coextensive with the floss or extend along only a portion of the floss.

Materials suitable for forming such barrier layers include water soluble materials that break down during use in the mouth (e.g., flossing) and release the components disposed therein, and materials that can be penetrated during flossing so as to expose the components therein and allow the components to contact and react with each other. Examples of such water soluble materials include those water soluble binders that are generally used in coatings for food products, e.g., hydrocollids, starches, chemically modified starches, alginates, pectins, gum arabic, gelatin, casein, soy protein, whey protein, wheat gluten, and zein.

Methods for incorporating a component into such layers are described generally, e.g., in U.S. Pat. Nos. 3,943,949 (Ashton et al.), 4,033,365 (Klepak et al.), 3,897,795 (Engel), and 3,771,536 (Dragan). Various methods may be used to apply the layers to the floss including, for example, hot melt coating, resin bath coating, spray coating, lick roll coating, and web coating. These methods are well known by those skilled in the art and are disclosed generally, for example, in U.S. Pat. Nos. 5,423,337 (Ahlert et al.) and 3,943,949 (Ashton et al.).

An alternate embodiment, in which dental hygiene article 30 includes components 32, 34 separated by barriers 36, 38 in the form of a layer 36 coated on floss 31 and a microcapsule 38 incorporated into layer 36, is shown in FIG. 3. Component 34 is encapsulated within microcapsule 38 and component 32 is coated on floss 31. Alternatively, microcapsule 38 may be coated on layer 36 and component 32 may be incorporated into barrier 36.

In another embodiment, a plurality of filaments 47, which form dental floss 46 and define lumen 41, function as a barrier surrounding component 42 as shown in FIG. 4. Filaments 47 inhibit components 42 and 44 from contacting and reacting with each other. Component 44 may be further separated from component 42 by the walls of microcapsule 48, i.e., a second barrier. The second barrier, however, may be in any form including, e.g., a water soluble layer surrounding the second component. Component 42 located in lumen 41 is released when filaments 47 separate or fray, e.g., during flossing.

In other embodiments, the dental hygiene article may include a floss having at least one filament 50 having openings 52 and 54, and at least one lumen 56 extending between the openings and containing component 58, as shown in FIG. 5. FIG. 5 depicts a single lumen filament, however, the filaments may have multiple lumens, e.g., two, three and four lumens. In addition, the number of lumens in each filament of a floss may also vary. For example, the floss may contain a combination of one or more single lumen, double lumen, triple lumen, and solid filaments. Each lumen can contain a different component. The walls of the filament(s) will fracture during flossing and release the component contained within each lumen. A component can also be coated on the exterior surface of the filament, as described above. Hollow filaments are commercially available, e.g., under the trade designations "Tynex Trilocular" and "Tynex Tetralocular" from DuPont of Wilmington, Del.

The dental hygiene article may also be in the form of a braided floss in which a plurality of filaments, e.g., hollow or solid filaments, are interlaced or woven together to form a hollow cylinder. The continuous wall of interlaced filaments (i.e., the wall of the cylinder) defines the lumen within the cylinder. Components may be placed in the lumen. Braided flosses are commercially available from Wardwell Braiding Machine Company of Central Falls, R.I.

Any method suitable for incorporating components into these lumens may be used including, e.g., injection, capillary action enhanced by pressurization, and vacuum suction, i.e., the components are pulled into the lumen using a vacuum. Opening 54 can be placed directly into the component and the component can be drawn into the lumen. Alternatively, the component can be directed into opening 54 by, for example, placing the component on top of a filtering device such as, e.g., a Buchner funnel, and tightly securing opening 54 near the stem of the funnel. The vacuum can be applied, for example, by attaching the vacuum directly to opening 52, or by suspending opening 52 in a vacuum flask and applying the vacuum to the side arm. Preferably the vacuum is applied simultaneously to a plurality of hollow filaments.

The vacuum pulls the component through each lumen and is applied for a period sufficient to fill the lumens to a desired height or length. The vacuum preferably suctions the component through the lumens but does not pull the component up along the length of the outer surface of the filament. When the vacuum is removed from the opening the component remains within the lumen.

The component can be in any form that will allow the component to be placed in and remain within the lumens of the filaments. Such forms include solutions, dispersions, microemulsions, gels, pastes, and powders. In addition, the component may be adsorbed onto the outer surface of microparticles, e.g., polystyrene microparticles or degradable microparticles, as described, for example, in U.S. Pat. No. 5,300,290 incorporated herein by reference, or encapsulated within microcapsules.

Suitable materials for use in forming the dental floss, including filaments 47 of the dental hygiene article shown in FIG. 4, are well known by those skilled in the art and include natural fibers, e.g., cotton and wool, synthetic polymer filaments, e.g., nylon, rayon, polyester, Dacron and acetate polymers, polypropylene, thermoplastic elastomers, e.g., Kratons (e.g., styrene-ethylene or styrene-butylene block copolymers), Pebax (e.g., polyether-polyamide block copolymers), and thermoplastic urethanes.

Components associated with the floss are selected so that when they are brought into contact with each other they will react to form a third component such as, e.g, a therapeutic agent, heat, a buffer, a gas (e.g., oxygen and carbon dioxide), or a film. Preferably the third component is capable of performing a function in the mouth, e.g., cleaning the mouth, remineralizing tooth enamel, protecting oral surfaces, and killing microorganisms.

One example of a suitable two component system is one in which the two components are selected so as to react with each other to form a therapeutic agent. An example of such a system is zinc bicarbonate and citric acid, which form zinc citrate. Zinc citrate has antibacterial, anticalculus and deodorizing properties.

Another example of a suitable two component system is one in which the two components are selected so as to react with each other to form a gas such as, e.g., carbon dioxide or oxygen. Bubbles of carbon dioxide and oxygen gas, when present in the mouth, provide an effervescence associated with a perceived feeling of cleaning and freshness, and also act to loosen deposits in the dental cavity, such as, e.g., food and plaque on teeth and gums. Flossing may be carried out so as to introduce the gas into the subgingival regions, which support anaerobic bacteria associated with periodontal disease. The presence of this gas, particularly oxygen, would compromise the environment necessary for these bacteria to thrive.

The two component system of zinc bicarbonate and citric acid can react to form carbon dioxide. A suitable two component system that reacts to form oxygen is peroxide and bicarbonate compounds.

Another example of a suitable two component system is one in which the two components are selected so as to react to form a remineralizing agent that will act to remineralize demineralized tooth enamel. One example of a suitable system for remineralizing the tooth surface is a system in which two components react to cause the precipitation of calcium and phosphate salts.

Another example of a suitable two component system is one in which the two components react to form a gel or a film. In situ film formation on surfaces of teeth and gingival tissue disrupts plaque formation. The film remains on the tooth surface and in the interdental spaces for extended periods, which prolongs the disruptive effect on plaque formation. Examples of suitable two component systems that react to form a film include: calcium salts (e.g., calcium acetate or calcium chloride) and hydrophilic colloidal polymers of (1–4) linked residues of $\beta$-D-mannopyranosyluronic acid and $\beta$-L-gulopyranosyluronic acids (e.g., alginates); and calcium salts and complex polysaccharides (e.g., pectins).

These film forming compositions may be used as a carrier for active agents, e.g., buffering agents, anti-microbial agents, and calcium-phosphate remineralization systems. The active agent may be included within the film forming components so that the active agent is disposed within the matrix of the film formed on the tooth surface. The film provides for the slow release of active agent over a period of time. In this way, an effective concentration of active agent can be maintained in the mouth for considerable periods after use of the floss.

Alternatively the components may be selected so as to react with each other to generate heat. Heat applied to the interproximal regions of the teeth and gums may kill various microorganisms. An example of a suitable two component system that generates heat includes the combination of calcium peroxide and a reducing agent such as, e.g., sodium metabisulfite, sodium sulfite, ascorbic acid, tocopherols, and phospholites.

The two components may also be selected so that they react to form a buffer, i.e., a solution having a neutral pH, e.g., a pH of about 7, or a pH that will not harm a tooth. The buffer acts to counter acids that may be present in the mouth, e.g., acids that are produced by the fermentation of dietary sugars and that may eventually demineralize the enamel surface. Materials suitable for forming a buffer within the mouth are known to those skilled in the art.

The first component and the second component are provided in a predetermined ratio selected so that when the components are released from the floss and contact each other they will form a third component. Preferably the first and second components are present in sufficient quantities so as to form the third component in quantities sufficient to effectively perform the desired function in the mouth. In addition, when the barrier is in the form of a microcapsule, a plurality of microcapsules containing components is contemplated.

Many different components, singly or in any suitable combination, can be included on the dental hygiene article. Suitable components and mixtures of components are those that are acceptable for use in the mouth, e.g., are non-toxic when provided in the amounts contemplated herein, and those that will not interfere with the ability of the two components to react to form a third component. These components may include, for example, anti-microbial agents, anti-gingivitis agents, anti-inflammatory agents, anti-caries agents, deodorizing agents, desensitizing agents, anti-calculus agents, anti-plaque agents, anti-viral agents, remineralization agents, effervescing agents, flavorants, scents, whitening agents, abrasives, pigments, dyes, and combinations thereof. The preferred concentration of additional components will vary depending on the intended function of the component and can be readily determined by the artisan.

Coloring agents, e.g., pigments and dyes, can be incorporated into the barrier along with each component so that each component is associated with a different color. When the components contact each other and react with each other, a third color is generated. The third color indicates to the user that a reaction is occurring or has occurred. Preferred coloring agents are those agents that are presently certified under the Food, Drug & Cosmetic Act for use in food and ingested drugs.

Suitable pigments include, e.g., synthetically derived pigments such as FD&C pigments, e.g., FD&C Blue #1 Lake, FD&C Blue #2 Lake, FD&C Yellow #5 Lake, FD&C Red #40 Lake; Erythrosin Lake; Amaranth Lake; Ponceau 4R Lake; Carmoisine Lake; natural pigments such as, e.g., titanium dioxide, Carmine Lake (blueish red), Carmine Lake (yellowish red), and Carmine Lake (purple); and pigments generated by converting a naturally derived dye to an aluminum or calcium-based salt.

Preferred dyes include dyes such as FD & C Red No. 3 (sodium salt of tetraiodofluorescein), FD & C Yellow No. 5 (sodium salt of 4-p-sulfophenylazo-1-p-sulfophenyl-5-hydroxypyrazole-3-carboxylic acid), FD & C Yellow No. 6 (sodium salt of p-sulfophenylazo-β-naphthol-6-monosulfonate), FD & C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD & C Blue No. 1 (disodium salt of dibenzyldiethyl-diaminotriphenylcarbinol trisulfonic acid anhydrite), FD & C Blue No. 2 (sodium salt of disulfonic acid of indigotin) and mixtures thereof.

The concentration of coloring agent in a unit area of the floss will affect the intensity of the color seen by the user when the color is released from the barriers. Thus, the coloring agent is preferably present in the floss in a concentration sufficient to provide a visually observable color change when the coloring agent is released from the barrier. The amount of coloring agent required will vary depending on the coloring agent used, the desired intensity, and the intended function of the coloring agent and can be readily determined by those skilled in the art.

Other embodiments are within the following claims. For example, an optional water insoluble layer, e.g., wax, may be coated over the floss, including the components and the barriers on the floss. The water insoluble layer functions as a barrier to moisture, e.g., the moisture that may be present during the manufacturing process and during storage of the dental hygiene article. For the first and second components to react with each other, the water insoluble layer must be physically altered so as to release the components from within the barriers and to allow water to access the barriers.

When the barrier is in the form of a microcapsule, the microcapsule may be modified to have a layer on its outer surface that surrounds a portion of the microcapsule, preferably the entire microcapsule. The layer is preferably impermeable, e.g., gas or liquid impermeable, to the component within the microcapsule. The impermeable layer inhibits loss of the component within the microcapsule due to evaporation or leaching. Preferably the impermeable layer inhibits loss of volatile active ingredients such as, e.g., flavor and scent oils. Materials suitable for forming an impermeable layer include, e.g., poly(methyl methacrylate), polystyrene, beeswax, carnauba wax, petroleum wax, polyhdroxylalkanoic acid, glycolipids, glycerides, phospholipids, and glycerol distearate.

Although a two component system has been described above, a multi-component system that is capable of reacting in the mouth to form one or more new components is also contemplated. Also, with the exception of the embodiments shown in FIG. 4 and FIG. 5, a monofilament dental floss can be used in place of the multifilament flosses described above. Although uniform distribution of the two component system across the entire length of the floss is preferred, the two components can be distributed in sections along a length of the floss.

What is claimed is:

1. A dental hygiene article comprising:
   a dental floss;
   a first component associated with said floss;
   a second component associated with said floss; and
   a first barrier constructed to separate said first component from said second component until flossing occurs,
   wherein said first and said second components are selected to react with each other to form an active agent selected from the group consisting of cleaning agents, agents for protecting teeth, agents for killing microorganisms, remineralizing agents, therapeutic agents, gases, films, buffers, heat, exclusion barriers, or a combination thereof when said first and said second components are combined.

2. The article of claim 1, wherein said barrier comprises a microcapsule and said first component is encapsulated within said microcapsule.

3. The article of claim 2, wherein said microcapsule is constructed to release said first component upon the application of a force to said floss to allow said first component to contact said second component.

4. The article of claim 2, wherein said microcapsule is water soluble.

5. The article of claim 2, further comprising a second barrier constructed to separate said second component from said first component.

6. The article of claim 5, wherein said second barrier comprises a water soluble binder associated with said second component in a manner to prevent said second component from contacting said first component.

7. The article of claim 6, wherein said second component is incorporated into said binder.

8. The article of claim 5, further comprising a first coloring agent encapsulated within said first microcapsule and a second coloring agent encapsulated within said second microcapsule.

9. The article of claim 1, wherein said barrier comprises a water soluble binder associated with said first component in a manner to prevent said first component from contacting said second component.

10. The article of claim 9, wherein first component is incorporated into said binder.

11. The article of claim 5, wherein said second barrier comprises a microcapsule and said second component is encapsulated within said microcapsule.

12. The article of claim 11, wherein said microcapsule is constructed to release said second component upon the application of a force to said floss to allow said second component to contact said first component.

13. The article of claim 1, further comprising a water insoluble barrier associated with said floss.

14. The article of claim 13, said water insoluble barrier being coated over said first and second components.

15. The article of claim 1, wherein one of said first and second components comprises a peroxide compound and the other component comprises a bicarbonate compound.

16. The article of claim 1, wherein said first and said second components are selected to react with each other to form a therapeutic agent.

17. The article of claim 1, wherein said first and said second components are selected to react with each other to form a gas.

18. The article of claim 1, wherein said first and said second components are selected to react with each other to form carbon dioxide.

19. The article of clam 1, wherein said first and said second components are selected to react with each other to form oxygen.

20. The article of claim 1, wherein said first and said second components are selected to react with each other to form a film.

21. The article of claim 1, wherein said first and said second components are selected to react with each other to form a buffer.

22. The article of claim 1, wherein said first and said second components are selected to react with each other to form an exclusion barrier.

23. The article of claim 1, wherein said first and said second components, upon reacting with each other, generate heat.

24. The article of claim 1, wherein one of said first and second components comprises a calcium salt and the other component comprises a phosphate salt.

25. The article of claim 1, wherein said first and said second components are further selected to react with each other to form a color.

26. The article of claim 1, wherein said first and said second components are selected to react with each other to form a remineralizing agent.

27. A dental hygiene article comprising:

a dental floss;

a first component associated with said floss, said first component comprising zinc bicarbonate;

a second component associated with said floss, said second component comprising citric acid;

a first barrier constructed to separate said first component from said second component until flossing occurs.

28. A method of manufacturing a dental hygiene article comprising:

associating a first component with a dental floss;

associating a second component with said dental floss;

selecting said first and second components to react with each other to form an active agent when said first and second components are combined, said active agent being selected from the group consisting of cleaning agents, agents for protecting teeth, agents for killing microorganisms, remineralizing agents, therapeutic agents, gases, buffers, exclusion barriers, and heat or a combination thereof; and separating said first and second components by providing a barrier constructed to separate said first and second components until flossing.

29. A method of flossing an interdental region of a mammal comprising:

placing a portion of a dental hygiene article in an interdental region, said dental hygiene article comprising a dental floss, a first component associated with said portion of said floss, a second component associated with said portion of said floss, and a barrier constructed to separate said first and said second components until flossing occurs, said first and said second components being selected such that they react with each other when said first and said second components are combined; and flossing said region with said portion of said dental hygiene article to cleanse the region.

30. A method of generating an active agent in the mouth comprising:

placing a portion of a dental hygiene article in an interdental region of a mammal, said article comprising a dental floss, a first microcapsule associated with said floss, a first component encapsulated within said first microcapsule, a second microcapsule associated with said floss, a second component encapsulated within said second microcapsule, said first and said second components capable of forming an active agent when brought into contact with each other; and flossing said region with said portions of said article to release said first and said second components, to allow said first and said second components to contact each other and react with each other to form an active agent selected from the group consisting of cleaning agents, agents for protecting teeth, agents for killing microorganisms, remineralizing agents, therapeutic agents, gases, buffers, exclusion barriers, and heat, or a combination thereof.

31. The method of claim 30, wherein said active agent comprises a therapeutic agent.

32. A dental hygiene article comprising:

a dental floss;

a first component associated with said floss;

a second component associated with said floss;

a first barrier comprising a wall defining a lumen, said first component being disposed within said lumen such that said wall separates said first component from said second component until flossing occurs;

said first and said second component being selected to react with each other when said first and said second components are combined.

33. The dental hygiene article of claim 32, further comprising a second barrier comprising a wall defining a second lumen, said second component being disposed within said second lumen.

34. The dental hygiene article of claim 32, further comprising a second barrier comprising a microcapsule, said second component being encapsulated in said microcapsule.

35. A dental hygiene article comprising:

a dental floss;

a first component associated with said floss;

a second component associated with said floss;

a binder layer associated with said first component such that said binder separates said first component from said second component until flossing occurs;

said first and said second component being selected to react with each other when said first and said second components are combined.

36. The article of claim 35, wherein said binder layer is water soluble.

37. The article of claim 35, wherein said binder layer is water insoluble.

* * * * *

UNITED STATES PATENT AND TRADEMARK OFFICE
CERTIFICATE OF CORRECTION

PATENT NO. : 5,937,874
DATED : August 17, 1999
INVENTOR(S) : Gordon G. Guay and Jean L. Spencer It is certified that error appears in the above-identified patent and that said Letters Patent is hereby corrected as shown below:

The following U.S. PATENTS DOCUMENTS were mistakenly omitted from the patent. Please insert:

| | | |
|---|---|---|
| -- 2,299,693 | 10/1942 | Green |
| 2,667,443 | 01/1954 | Ashton |
| 3,942,539 | 03/1976 | Corliss et al. |
| 4,776,538 | 10/1988 | Lorch |
| 4,819,675 | 04/1989 | Wilkinson et al. |
| 5,165,913 | 11/1992 | Hill et al. |
| 5,423,337 | 06/1995 | Ahlert et al. |
| 5,732,721 | 03/1998 | Pelok |
| 2,386,252 | | Mendelsonhn |
| 2,748,781 | 06/1956 | Collat |
| 3,771,536 | 11/1973 | Dragan |
| 3,897,795 | 08/1975 | Engel |
| 3,943,949 | 03/1976 | Ashton et al. |
| 3,991,766 | 11/1976 | Schmitt et al. |
| 4,033,365 | 07/1977 | Klepak et al. |
| 4,071,614 | 01/1998 | Grimm, III |
| 4,175,326 | 11/1979 | Goodson |
| 4,459,277 | 07/1984 | Kosti |
| 4,597,959 | 07/1986 | Barr |
| 4,678,814 | 07/1987 | Rembaum |
| 4,764,377 | 08/1988 | Goodson |
| 4,780,320 | 10/1988 | Baker |
| 4,828,955 | 05/1989 | Kasai et al. |
| 4,871,352 | 10/1989 | Tran |
| 4,904,479 | 02/1990 | Illum |

UNITED STATES PATENT AND TRADEMARK OFFICE
CERTIFICATE OF CORRECTION

PATENT NO. : 5,937,874  
DATED : August 17, 1999  
INVENTOR(S) : Gordon G. Guay and Jean L. Spencer It is certified that error appears in the above-identified patent and that said Letters Patent is hereby corrected as shown below:

U.S. PATENT DOCUMENTS cont'd:

| | | |
|---|---|---|
| 4,911,927 | 03/1990 | Hill et al. |
| 4,919,939 | 04/1990 | Baker |
| 4,941,487 | 07/1990 | Van Beneden |
| 4,971,785 | 11/1990 | Wilson et al. |
| 4,980,154 | 12/1990 | Gordon -- |

Signed and Sealed this

Fifth Day of February, 2002

Attest:

JAMES E. ROGAN  
Attesting Officer  *Director of the United States Patent and Trademark Office*